(12) United States Patent
Odaka et al.

(10) Patent No.: US 6,175,580 B1
(45) Date of Patent: Jan. 16, 2001

(54) APPARATUS AND METHOD FOR DETECTING FAILURES IN LASER TRANSMITTING TUBE AND LASER DEVICE

(75) Inventors: Masaki Odaka; Akira Yuba, both of Kyoto (JP)

(73) Assignee: J. Morita Manufacturing Corporation, Kyoto (JP)

( * ) Notice: Under 35 U.S.C. 154(b), the term of this patent shall be extended for 0 days.

(21) Appl. No.: 09/221,811

(22) Filed: Dec. 29, 1998

(30) Foreign Application Priority Data

Dec. 29, 1997 (JP) .................................................. 9-367659

(51) Int. Cl.[7] ...................................................... G02B 5/14
(52) U.S. Cl. ................................................ 372/33; 372/61
(58) Field of Search ........................................ 372/33, 61

(56) References Cited

U.S. PATENT DOCUMENTS 4,543,477  9/1985  Doi et al. .

FOREIGN PATENT DOCUMENTS

| 3601118 | 3/1989 | (DE) . |
|---|---|---|
| 19514118 | 1/1995 | (DE) . |
| 19615615 | 1/1997 | (DE) . |

*Primary Examiner*—Leon Scott, Jr.
(74) *Attorney, Agent, or Firm*—Koda & Androlia

(57) ABSTRACT

A device for detecting failures in a laser transmitting passage includes an inner tube (80) made from an optical hollow waveguide and having a first space (122) through which laser is transported, an outer tube (78) surrounding and extending along the inner tube, and a detector which recognizes a first condition in which the first space is fluidly disconnected from the second space and a second condition in which the first space is fluidly connected to the second space. The first and second conditions can be determined from a pressure, flow rate, gas concentration, ingredient of gas, or temperature in first or second space.

23 Claims, 5 Drawing Sheets

APPARATUS AND METHOD FOR DETECTING FAILURES IN LASER TRANSMITTING TUBE AND LASER DEVICE

FIELD OF THE INVENTION

The present invention relates to a method and apparatus for detecting failures in a laser transmitting tube. Further, the present invention relates to a laser device which incorporates such method and apparatus.

BACKGROUND OF THE INVENTION

Laser has been used not only in industrial devices but also in many medical and dental devices. Generally, each of medical and dental devices using laser includes a laser generator for generating laser, a hand instrument for guiding and then emitting laser toward a desired surgical site, and a passage or tube connecting between the laser generator and the hand instrument for transmitting laser from the laser generator to the hand instrument. Typically, the laser transmitting tube is defined from a flexible optical fiber around which is covered with a flexible protecting tube, allowing the laser to be projected onto a desired surgical site and at a desired angle.

As such, since the laser transmitting tube is made of flexible optical fiber, it can be bent sharply as much as the optical fiber would eventually be stressed to damage. The damage of the transmitting tube may result in that leaked laser burns out a corresponding portion of the outer protecting tube. This fails to ensure that a desired amount of laser would be emitted out of the hand instrument.

To solve this problem, various methods have been proposed for detecting failures of the laser transmitting tube. For example, Japanese Utility Model Publication No. 60-21046 discloses a failure detecting device. In this device, a wire is herically wound along the laser transmitting tube. With the device, once the laser transmitting tube is broken, leaked laser melts a corresponding portion of the wire, which is electrically detected.

Also, Japanese Patent Laid-Open Publication No. 60-60531 discloses another failure detecting device. In this device, a cable made from a plastic fiber is mounted adjacent the laser transmitting tube. The device includes a detector capable of detecting failures of the laser transmitting tube. With the device, once the laser transmitting tube is broken, the leaked laser melts a corresponding portion of the plastic fiber, which is detected by the detector.

Further, Japanese Utility Model Publication No. 58-7365 discloses another failure detecting device. The device includes a photodiode positioned adjacent an outlet of the laser transmitting passage. This allows the device to detect the failures or damages of the laser transmitting passage from a variation of the intensity of the laser emitted out of the outlet.

Furthermore, Japanese Patent Laid-Open Publication NO. 56-40737 discloses another failure detecting device. In this device, an outlet of the laser transmitting passage is applied with a coating capable of increasing an intensity of reflected laser and a detector for detecting the reflected laser. With the device, the detector detects a variation of the intensity of the reflected laser, allowing it to detect failures of the laser transmitting passage.

SUMMARY OF THE INVENTION

The present invention provides a method and apparatus for detecting failures of a laser transmitting passage with specific techniques newly employed therein. Also, the present invention provides a laser device which incorporates such method and apparatus.

Briefly described, a failure of the laser transmitting passage is detected with the use of a fluid running in the passage. Specifically, an apparatus for detecting failures in a laser transmitting passage includes an inner tube having therein a first space through which laser is transmitted, an outer tube surrounding and extending along the inner tube and thereby defining a second space between inner and outer tubes, and a detector which recognizes a first condition in which the first space is fluidly disconnected from the second space and a second condition in which the first space is fluidly connected to the second space. Preferably, the inner tube is an optical hollow waveguide.

In another aspect of the present invention, the detector recognizes the first and second conditions from a change of condition occurred either in the first space or in the second space.

Also, in another aspect of the present invention, the condition may relate to any one of following items;

a pressure in the first space or in the second space;

a flow rate of gas transported in the first space or in the second space;

a concentration of gas contained in the first space or in the second space;

an ingredient of gas contained in the first space or in the second space; and a temperature in the first space or in the second space.

Further, in another aspect of the present invention, the apparatus includes an interlock that prohibits laser from being supplied through the first space when the detector has detected the second condition.

A method for detecting failures in a laser transmitting tube of the present invention includes the steps of detecting a change of condition of either interior or exterior of the laser transmitting tube and detecting that the laser transmitting tube has been damaged from the change of condition. The condition relates to a pressure, a flow rate of gas, a concentration of gas, an ingredient of gas, or a temperature, either in the first space or in the second space.

With the apparatus and method of the present invention, once the laser transmitting tube is damaged, the first (inner) space is fluidly connected with the second (outer) space. The detector detects that the first and second spaces have been connected to each other from, for example, a change of condition such as a pressure, a flow rate of gas, a concentration of gas, an ingredient of gas, or a temperature, either in the first space or in the second space. Further, with the embodiment in which the interlock is provided, once the first and second spaces are connected to each other, the interlock prohibits the generation of laser.

As such, according to the present invention, similar to the conventional devices, the damage of the laser transmitting tube can be detected.

DETAILED DESCRIPTION OF THE PREFERRED EMBODIMENTS

Figure 1:
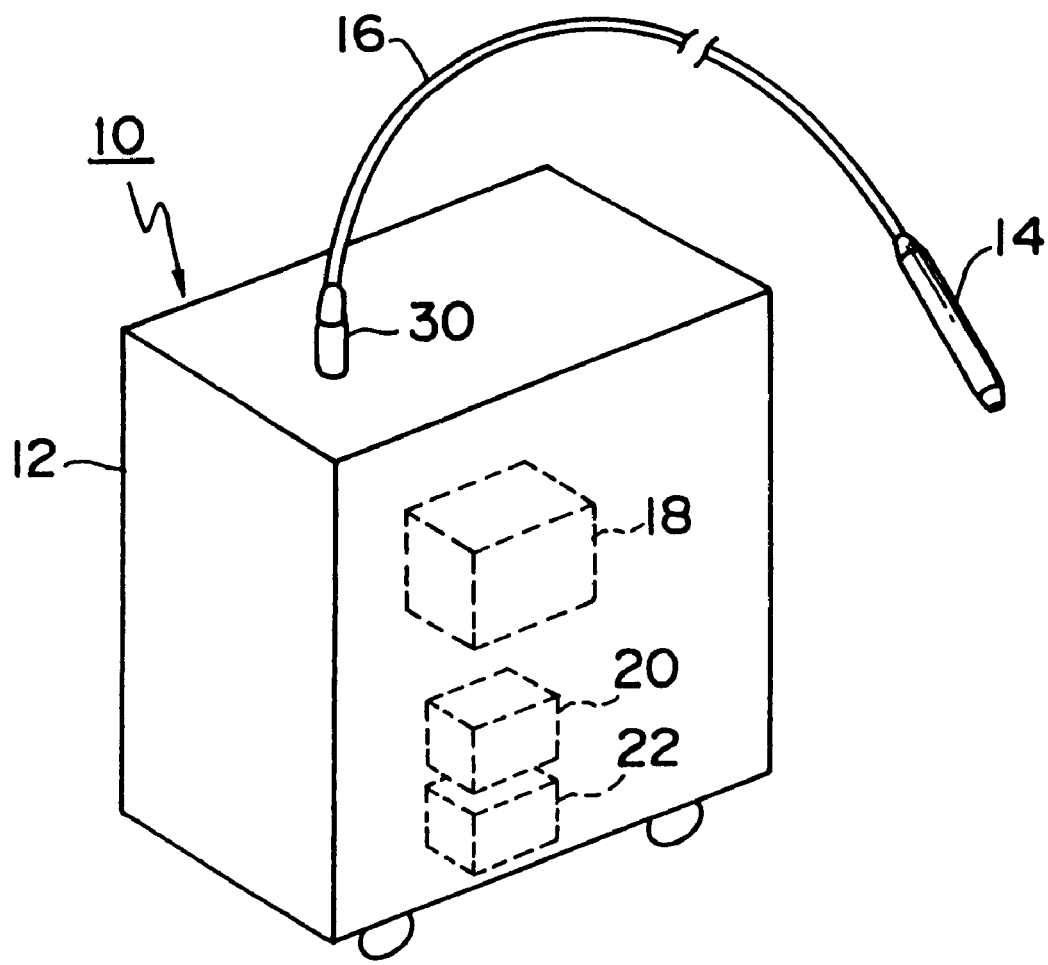
FIG. 1 is a perspective view of a medical device of the present invention, in which an apparatus for detecting failures of a laser transmitting tube is incorporated therein.

Referring to the drawings, particularly in FIG. 1, there is shown an outline of a medical device that uses laser for treatment, generally indicated by reference numeral 10. It should be noted that the term "medical device" includes not only medical device but also dental device throughout this specification. It should also be noted that the present invention is not limited to the medical device and it is equally applicable to various devices that use laser.

The medical device 10 has a laser unit 12 in which laser is generated, a hand instrument 14 that an operator can hold it to direct laser toward a desired surgical site, and a flexible supply line 16 that connects between the laser unit 12 and the hand instrument 14 for transmitting laser from the laser unit 12 to the hand instrument 14. The laser unit 12 includes a laser generator 18 for generating laser and pumps 20 and 22 for feeding air and water, respectively, through the flexible supply line 16 to the hand instrument 14. Such airs and water are fed through respective tubes mounted in the supply line 16, which will be described in detail hereinafter.

Figure 2:
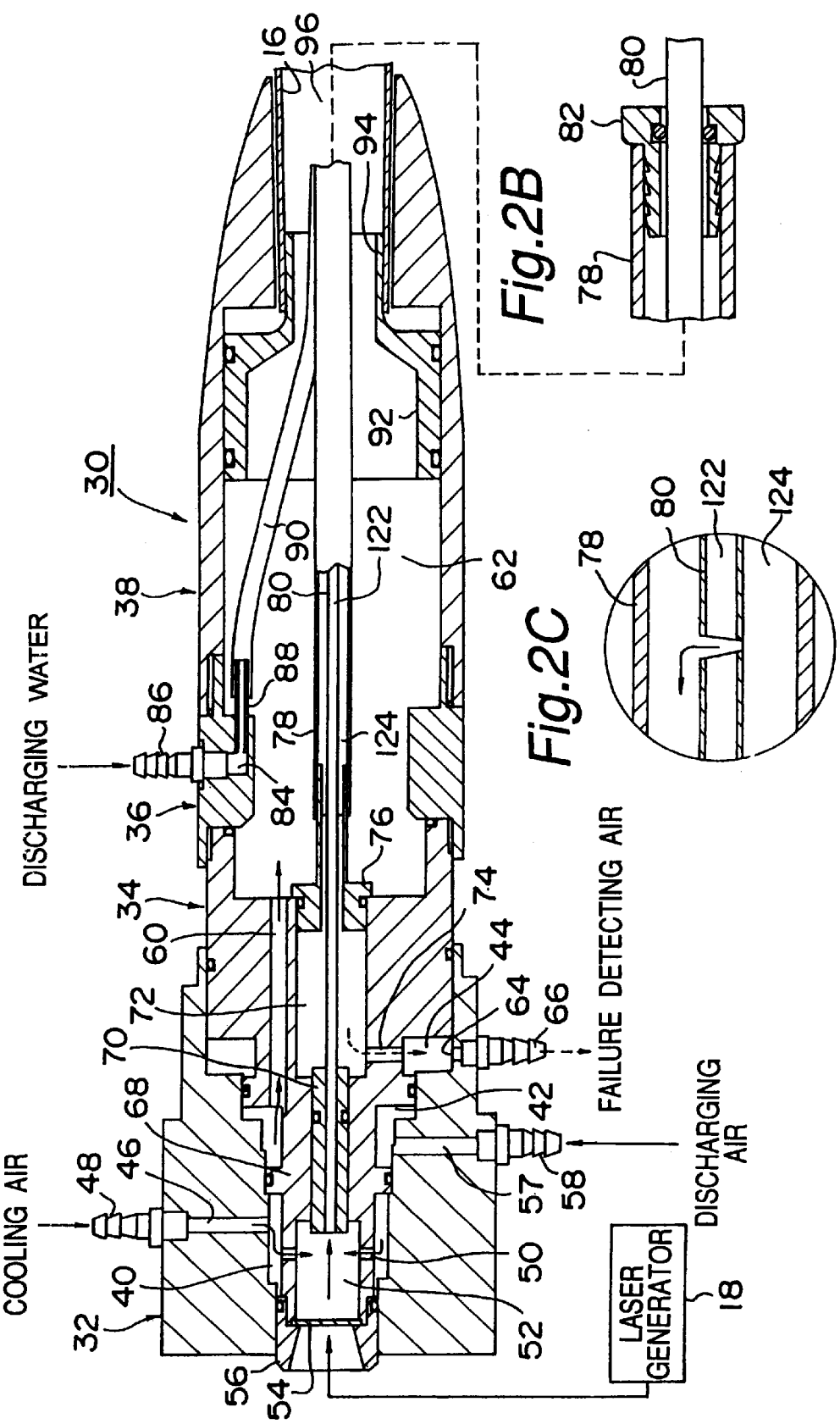
FIG. 2A is an enlarged cross sectional view of a connecting portion of a laser unit and a flexible supply line, showing a structure of the apparatus for detecting failures of the laser transmitting tube.
FIG. 2B is an enlarged cross sectional view of a seal structure provided at a distal end of a protection tube.
FIG. 2C is an enlarged cross sectional view, showing a damaged portion of the laser transmitting tube.

FIG. 2 shows a cross section of a connecting unit 30 of the laser unit 12 and the flexible supply line 16. The connecting unit 30 has four cylindrical connecting members; first connector 32, second connector 34, third connector 36, and fourth connector 38, connected in series in this order. Preferably, an O-ring is provided at each contact region of between opposing surfaces of the neighboring connectors, forming an airtight seal therebetween.

The first connector 32 is secured to the laser unit 12 at its proximal end positioned adjacent the laser unit 12. The second connector 34 is inserted at its proximal end into the distal end of the first connector 32. An inner peripheral surface of the first connector 32 is formed with a plurality of steps each extending circumferentially. Also, an outer peripheral surface of the second connector 34, inserted in the first connector 32, is formed with a plurality of steps each extending circumferentially. The circumfrential steps of inner and outer surfaces cooperate to each other, forming three separate circumferential passages between the opposing surfaces of the connectors 32 and 34; passage 40 for drying and cooling air, passage 42 for discharging air, and passage 44 for failure detecting air, positioned in series in this order.

For the passage 40 of drying and cooling air, the first connector 32 is formed with a passage 46 extending radially. The radial passage 46 is fluidly connected at its inner end to the passage 40 and at its outer end to a connecting piece 48 through which drying and cooling air is supplied. The second connector 34, on the other hand, is formed with a plurality of passages 50 each extending radially. Through the passages 50, a passage 52 formed adjacent the distal end of the second connector 34 is fluidly connected with the passage 40 positioned outside thereof. A proximal end of the passage 52 is closed by a transparent plate 54 through which laser can pass. Preferably, the transparent plate 54 is secured between the proximal end of the second connector 34 and a cylindrical member 56 fitted in the proximal end opening of the first connector 32.

For the passage 42 of discharging air, the first connector 32 is formed with a passage 57 extending radially. The passage 57 is fluidly connected at its inner end with the passage 42 for discharging air and at its outer end with a connecting piece 58 through which the air is supplied. The second connector 34, on the other hand, is formed with an air passage 60 extending longitudinally and parallel to a longitudinal axis thereof. The passage 60 is fluidly connected at its proximal end with the passage 42 of discharging air and at its distal end with another air passage 62 defined in the third and fourth connectors 36 and 38.

For the passage 44 of air to be used for detecting failures, the first connector 32 is further formed with a passage 64 extending radially. The passage 64 is fluidly connected at its inner end with the passage 44 for drying and cooling air and at its outer end with a connecting piece 66 through which failure detecting air is discharged to the atmosphere.

The second connector 34 includes a reduced portion 68, defining a distal end of the proximal passage 52, in which a cylindrical tube or ferrule 70 is inserted. The ferrule 70 is sealed airtightly with the inner surface of the reduced portion 68 by a suitable sealing member such as O-ring. A central and distal passage 72 is formed adjacent the reduced portion 68 but remote from the proximal passage 52. The passage 72 is fluidly connected with the circumferential passage 44 radially spaced therefrom through a passage 74 formed in the second connector 34.

The distal end of the passage 72 in the second connector 34 is connected with a connecting tube 76 engaged in the passage 72. The proximal end of the tube 76 is connected with a protection tube 78 in which a laser transmitting tube 80 connected at its proximal end with the distal end of the ferrule 70. Preferably, the laser transmitting tube 80 is an optical hollow waveguide disclosed in the U.S. Pat. No. 5,729,646 which is entirely incorporated herein by refernce. The protection tube 78 together with the laser transmitting passage 80 is extended through the interior of the flexible supply line 80 or tube into the hand instrument 14.

Referring to FIG. 2B, a distal end of the protection tube 78 is closed by a packing tube 82 mounted on the laser transmitting tube 80. Preferably, an airtight seal such as O-ring is provided between the packing tube 82 in the form of ring and the laser transmitting tube 80. Advantageously, this allows the packing tube 82 to move slightly in the longitudinal direction relative to the laser transmitting tube 80 when the flexible supply line 16 including the laser transmitting tube 80 would be curved, preventing both the laser transmitting tube 80 and the protection tube 78 from being stressed too much.

The third connector 36 is formed with a passage 84 connecting between interior and exterior of the connector 36. Also, the passage 84 is connected at its outer end with a connecting piece 86 and at its inner end with another connecting piece 88. The connecting piece 86 is in turn connected with a water source for supplying water to be discharged from the hand instrument 14. Another connecting piece 88, on the other hand, is connected with a water supply tube 90 extending through the interior of the flexible supply line 16 into the hand instrument 14, together with the laser transmitting tube 80.

The fourth connector 38 includes therein a connecting ring 92. Preferably, the connecting ring 92 is so sized and shaped that it can fit with the connector 38. Specifically, portions of the connecting ring 92 have respective outer diameters being substantially identical to inner diameters of the corresponding portions of the connector 38. Also, an airtight seal such as O-ring is provided between the connector 38 and the connecting ring 92. The connecting ring 92 is formed at its distal end with a reduced tube connecting portion 94 to which the proximal end of the flexible supply line 16 is connected airtightly, allowing the air passage 62 in the connector 30 is fluidly connected with the interior 96 of the flexible supply line 16.

Figure 3:
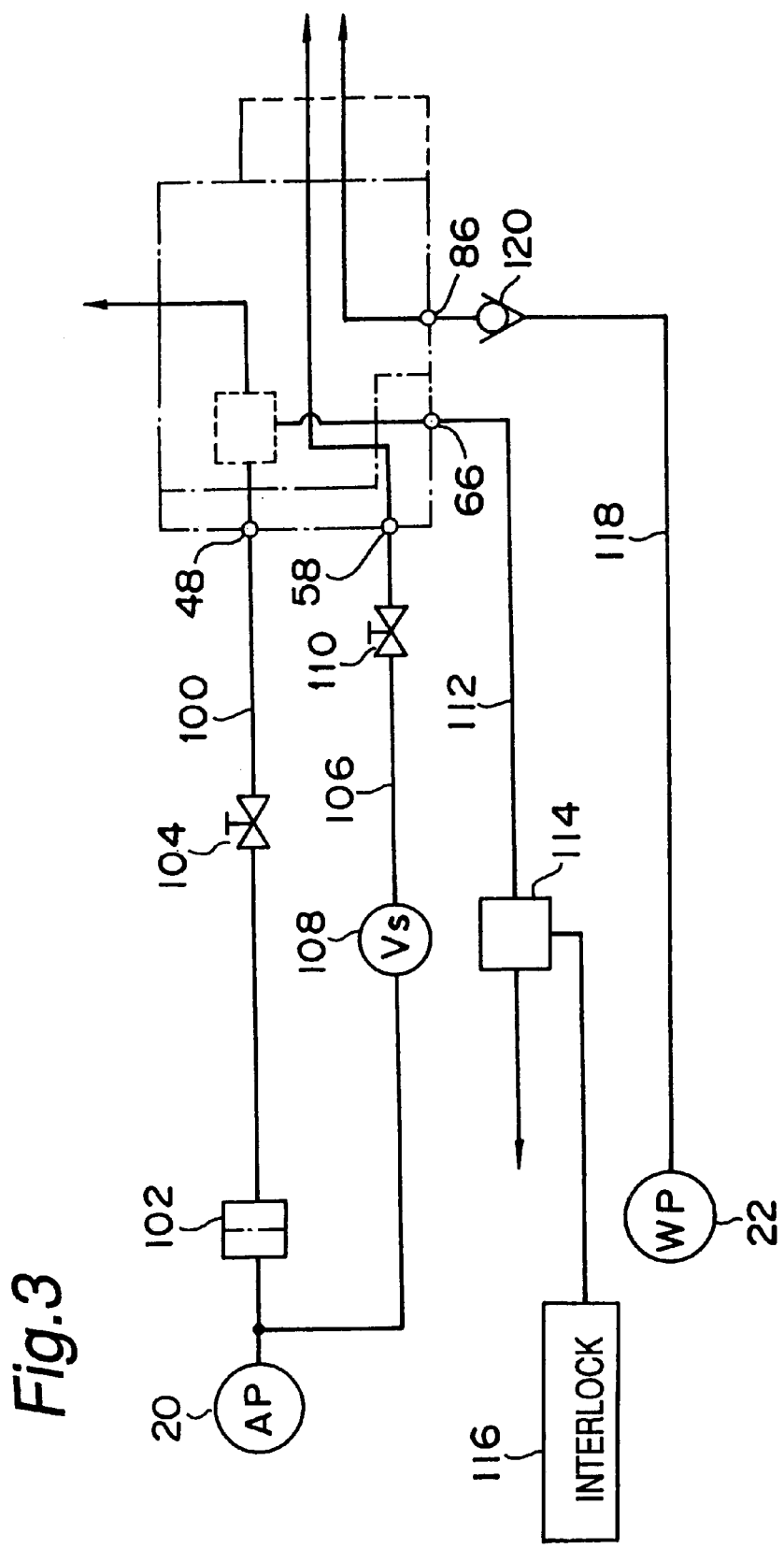
FIG. 3 is a piping diagram of the medical device for transporting drying and cooling air, discharging air, and discharging water.

FIG. 3 shows a piping diagram of drying and cooling air, discharging air, and discharging water. As shown in the drawing, the connecting piece 48 is connected through a passage 100 to an air supply pump 20. Preferably, the passage 100 has a dryer 102 for dehumidifying and then drying air to be fed from the pump 20 and a flow rate control valve 104. The dryer 102 may be a so-called membrane dryer which includes membrane or membranes capable of filtering off moisture from air.

The connecting piece 58 is connected to the air pump 20 through a tube 106 having an ON/OFF control valve 108 and a flow rate control valve 110. Also, the connecting piece 66 is connected to a tube 112 having a flowmeter 114. The flowmeter 114 is electrically communicated with an interlock 116 for switching off the laser generator 18. Further, the connecting piece 86 is connected to the water pump 22 through a tube 118 having a check valve 120 for preventing the water from being transported in the reverse direction when water and air outlets of the hand instrument would bring into physical contact with the surgical site or something and thereby the pressure of the water passage would increase too much.

In operation of the medical device 10 so constructed, as shown in FIGS. 1 and 2, laser generated at the laser generator 18, as required, is transmitted through the transparent plate 54, passage 52 into the laser transmitting tube 80 and then into the hand instrument 14, and finally projected from, for example, a laser probe mounted at a tip portion of the hand instrument 14 onto a desired surgical site.

As shown in FIG. 3, drying and cooling air is fed from the pump 20 into the passage 106, dehumidified and dried by the dryer 102, metered to a desired rate by the control valve 110, and then supplied to the connecting piece 48. As best shown in FIG. 2, after passing through the connecting piece 48, drying and cooling air is transported through the passages 46, 40, 50 and 52, then through the laser transmitting tube 80, and finally into a predetermined portion of the hand instrument 14, thereby cooling and drying the portion which would otherwise be heated by the transmission of the laser.

Referring back to FIG. 3, discharging air, when the ON/Off control valve 108 is opened, is fed from the pump 20 into the tube 100 where it is metered to a predetermined rate by the flow rate control valve 110 and then into the connecting piece 58. Subsequently, as best shown in FIG. 2, discharging air is conveyed through passages 57, 42, 60 and 62, passage 96 in the flexible supply line 16, and further another passage (not shown) formed in the hand instrument 14 and finally discharged from the tip portion of the hand instrument.

Referring back again to FIG. 3, discharging water is fed from the pump 22 through the passage 118 and check valve 120 and then into the connecting piece 86. As best shown in FIG. 2, after passing through the connecting piece 86, the water is further transported through passage 84, connecting piece 88, water supply tube 90, and a passage (not shown) formed in the hand instrument 14 and finally sprayed with the discharging air.

The flexible supply line 16 is subject to be bent or stretched by the operator of the device, which is occurred so often in the normal treatment of the device 10. Unfortunately, if the supply line 16 is curved or stretched in part too much, the laser transmitting tube 80 can damage to crack, which is shown in FIG. 2C. This causes that an interior (first space) 122 of the laser transmitting tube 80 is fluidly connected through the cracks with an exterior of the laser transmitting tube 80, i.e., an interior (second space) 124 of the protection tube 78. This allows drying and cooling air running in the space 122 of the laser transmitting tube 80 leaks out into the exterior space 124. The leaked air travels through the passages 72, 74, and 44, connecting piece 66, and tube 112 and sensor 114 (see FIG. 3) into the atmosphere. Once the sensor 114 senses air, the interlock 116 instructs the laser generator 18 to stop further laser generation.

In view of this, according to the medical device 10, when the laser transmitting tube 80 is damaged, it is detected positively and thereby further generation of laser is stopped, preventing the partial burnings of the protection tube 78 and further flexible line 16 which would otherwise be caused by the leaking of laser. This further prevents human beings from being damaged by the leaking of the laser.

Although in the previous embodiment the ferrule 70 and the connecting tube 76 are separated through the passage 72, these members may be integrated into one member. In this case, a passage connecting the space 124 and the passage 74 may be formed in the integrated member.

Figure 4:
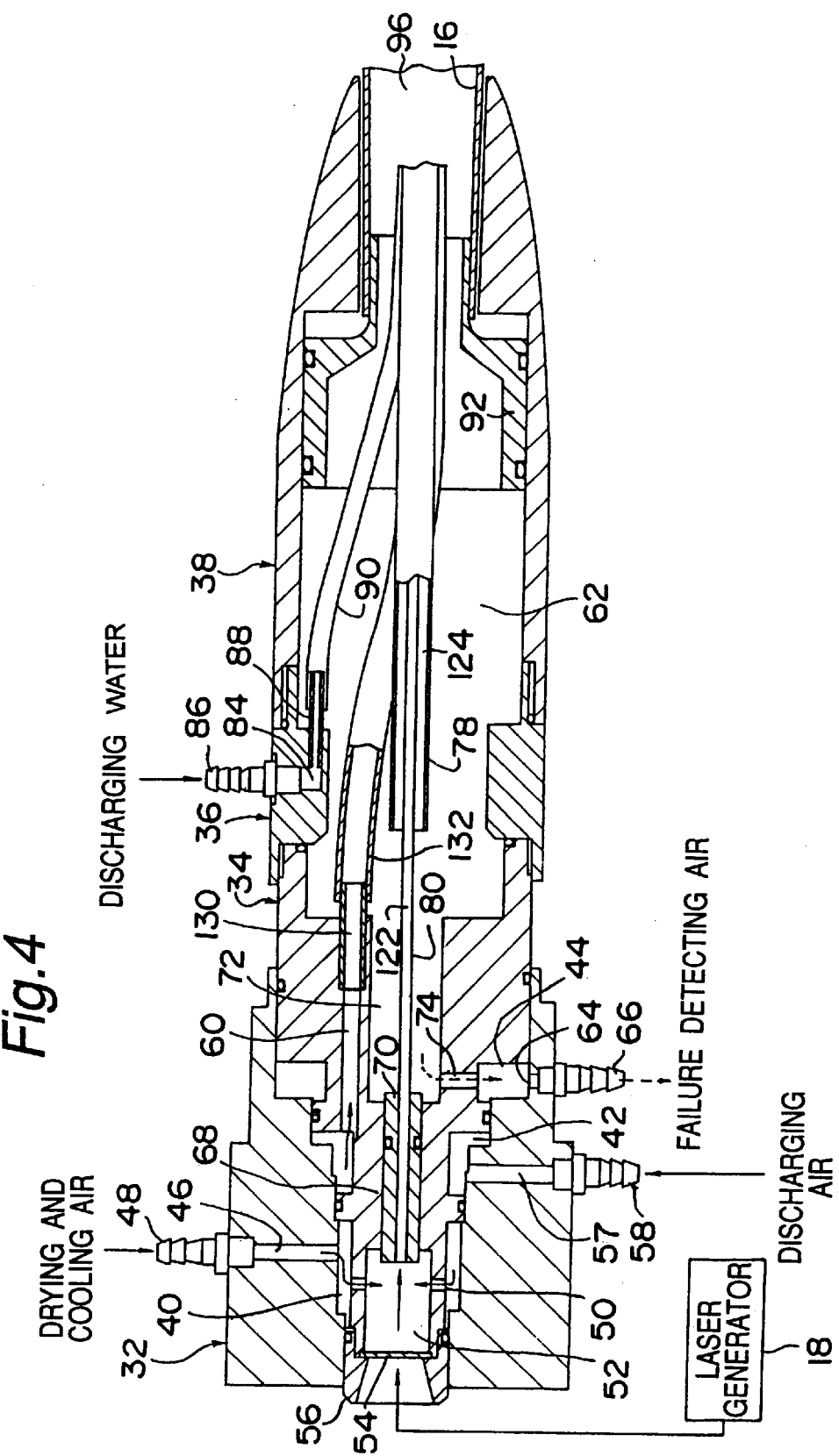
FIG. 4 is a an enlarged cross sectional view of a connecting portion of the laser unit and the flexible supply line of the second embodiment of the present invention.
Figure 5:
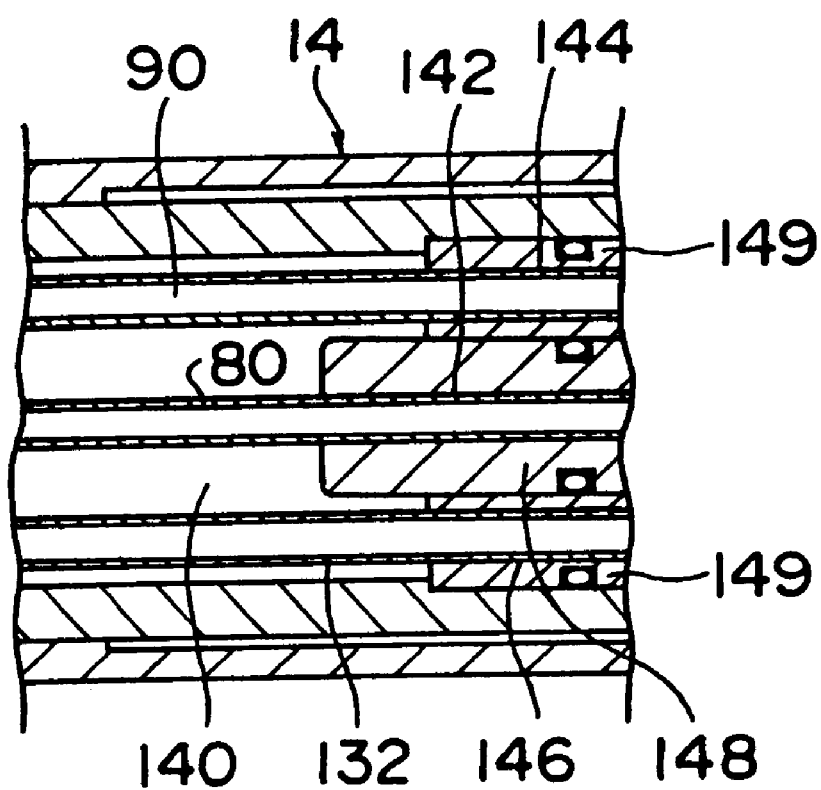
FIG. 5 is an enlarged cross sectional view of a portion of a hand instrument, showing a sealing structure for sealing a distal end of a space surrounding the laser transmitting tube of the second embodiment.

Also, although the laser transmitting tube 80 is surrounded by the protection tube 78, the connecting tube 76, and ring-like packing 82 so that the passage in the protection tube 78 is disconnected from the passage 62 formed in the third and fourth connectors 36 and 38, the passage 62 may be used as the second space. In this instance, as shown in FIG. 4, a distal end of the passage 60 for transporting discharging air may be connected to a connecting tube 130 which in turn connected at its distal end to another tube 132 for discharging air. Also, the distal end of the passage 62 may be closed in the hand instrument 14. To this purpose, as shown in FIG. 5, the hand instrument 14 includes partitions 148 and 149 having passages 142, 144, and 146 through which tubes 80, 90, and 132 passes, respectively. Also, a suitable sealing member such as O-ring may be provided between the tubes 80, 90, and 132 and opposing portions of the partition 148. This ensures that a passage 140 fluidly connected with the passage 62 is positively sealed at its distal end.

Therefore, the device ensures that air leaked from the laser transmitting tube 80 travels from the interior 124 of the protection tube 78 through passages 62, 72, 74, and 44, connecting piece 66, and tube 112 and flowmeter 114 (see FIG. 3) into the atmosphere. Once having detected the leaking of air, the interlock 116 de-energizes the laser generator 18.

It should be noted that, when compared the embodiments shown in FIGS. 1 and 4, it appears that the first embodiment is advantageous over the second embodiment because no tube for the discharging air is required in the flexible supply line 16.

In the previous embodiments, the failures of the laser transmitting tube 80 is detected by the detection of the airflow which would be caused by the damage of the laser transmitting tube 80. The present invention is not limited thereto, and the failures of the laser transmitting tube 80 may be detected by any environmental change in the interior and/or exterior of the laser transmitting tube 80. For example, either of the interior or exterior may be pressurized or depressurized to form a pressure difference between the interior and exterior. In this instance, by detecting a pressure change either in interior or in exterior of the laser transmitting tube, it is determined that the laser transmitting tube has been damaged. To pressurize the interior of the laser transmitting tube 80, air to be discharged can be transported therethrough. In this instance, the interior as well as the inlet and outlet of the laser transmitting tube can be cooled by the air, and in turn the air can be warmed.

Alternatively, a suitable gas having specific chemical component or components harmless to human beings may be transported or accommodated either in interior or in exterior of the laser transmitting tube. In this instance, the damage of the laser transmitting tube can be recognized, using a suitable detector, through the detection of the chemical component of the gas which would leak into the opposite space or the detection of a change of the concentration of the gas due to the damage of the laser transmitting tube.

Further, airs having different temperatures may be transported or accommodated in the interior and exterior of the laser transmitting tube, respectively. In this instance, the damage of the laser transmitting tube can be recognized, using a suitable thermometer, through the detection of the temperature change which would be caused by the leaking of the air.

The present application is based upon Japanese Patent Application No. 09-368659, which is incorporated herein by reference.

In view of above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. An apparatus for detecting failures in a laser transmitting tube, comprising:
    an inner tube having therein a first space through which laser is transmitted;
    an outer tube surrounding and extending along said inner tube and thereby defining a second space between said inner and outer tubes; and
    a detector detecting a first condition in which said first space is fluidly disconnected from said second space and a second condition in which said first space is fluidly connected to said second space.

2. An apparatus as set forth in claim 1, wherein said inner tube is an optical hollow waveguide.

3. An apparatus as set forth in claim 1, wherein said detector recognizes said first and second conditions from a change of condition occurred in said first space or in said second space.

4. An apparatus as set forth in claim 3, wherein said change of condition is a change of flow rate of gas flowing in said first or second space to which said detector is fluidly connected.

5. An apparatus as set forth in claim 3, wherein said change of condition is a change of pressure in said first or second space to which said detector is fluidly connected.

6. An apparatus as set forth in claim 3, wherein said change of condition is a change of concentration of gas in said first or second space to which said detector is fluidly connected.

7. An apparatus as set forth in claim 3, wherein said change of condition is a change of ingredient of gas in said first or second space to which said detector is fluidly connected.

8. An apparatus as set forth in claim 3, wherein said change of condition is a change of temperature in said first or second space to which said detector is fluidly connected.

9. An apparatus as set forth in claim 1, further comprising an interlock that prohibits said laser from being supplied through said first space when said detector has detected said second condition.

10. A method for detecting failures in a laser transmitting tube, comprising the steps of:
    detecting a change of condition of interior or exterior of said laser transmitting tube; and
    detecting that said laser transmitting tube has been damaged from said change of condition.

11. A method as set forth in claim 10, wherein said change of condition is a change of flow rate of gas flowing in said first or second space to which said detector is fluidly connected.

12. A method as set forth in claim 11, wherein said change of condition is a change of pressure in said first or second space to which said detector is fluidly connected.

13. A method as set forth in claim 11, wherein said change of condition is a change of concentration of gas in said first or second space to which said detector is fluidly connected.

14. A method as set forth in claim 11, wherein said change of condition is a change of ingredient in said first or second space to which said detector is fluidly connected.

15. A method as set forth in claim 11, wherein said change of condition is a change of temperature in said first or second space to which said detector is fluidly connected.

16. An apparatus for detecting failures in a laser transmitting tube, comprising:
    an outer tube;
    an inner tube, inserted in said outer tube, having a first space through which laser is transmitted and cooperating with said outer tube to define a second space between said inner and outer tubes; and
    a detector fluidly connected with said first or second space for detecting whether said first space is fluidly connected with said second space.

17. An apparatus as set forth in claim 16, wherein said inner tube is an optical hollow waveguide.

18. An apparatus as set forth in claim 16, wherein said detector detects a change of condition of said first or second space fluidly connected thereto.

19. An apparatus as set forth in claim 16, wherein said change of condition is a change of flow rate of gas flowing in said first or second space to which said detector is fluidly connected.

20. An apparatus as set forth in claim 16, wherein said change of condition is a change of pressure in said first or second space to which said detector is fluidly connected.

21. An apparatus as set forth in claim 16, wherein said change of condition is a change of concentration of gas in said first or second space to which said detector is fluidly connected.

22. An apparatus as set forth in claim 16, wherein said change of condition is a change of ingredient of gas in said first or second space to which said detector is fluidly connected.

23. An apparatus as set forth in claim 16, wherein said change of condition is a change of temperature in said first or second space to which said detector is fluidly connected.

* * * * *